United States Patent [19]

Henderson et al.

[11] Patent Number: 5,645,844
[45] Date of Patent: Jul. 8, 1997

[54] NEGATIVELY CHARGED CHITOSAN DERIVATIVE SEMIOCHEMICAL DELIVERY SYSTEM

[75] Inventors: Susan Elizabeth Henderson, Wellington; Dennis Thomas Curran; Clive M. Elson, both of Halifax, all of Canada

[73] Assignee: Chitogenics, Inc., Cedar Knolls, N.J.

[21] Appl. No.: 483,996

[22] Filed: Jun. 7, 1995

[51] Int. Cl.$^6$ ..................................................... A01N 25/10
[52] U.S. Cl. .......................... 424/405; 424/409; 424/410; 424/411; 424/84; 424/485; 424/538
[58] Field of Search ............................... 536/20; 424/538, 424/547, 405, 409–411, 84

[56] References Cited

U.S. PATENT DOCUMENTS

| | | | |
|---|---|---|---|
| 3,879,376 | 4/1975 | Vanlerberghe et al. | 260/211 R |
| 4,619,995 | 10/1986 | Hayes | 536/20 |
| 5,466,461 | 11/1995 | della Valle et al. | 424/423 |

OTHER PUBLICATIONS

Kydonieus, Agis ed. (1982) Insect Suppression with Controlled Release Pheromone Systems. Boca Ratan: CRC. 1:136,137,139,146,217.

Audemard H., (1988), "Confusion Sexuelle avec des Phéromones en Europe De L'Quest", *Agric. Ecosyst. Environ.*, 21, pp. 101–110.

Brown, D.F. et al., (1992), "Emission Characteristics of a Polyethylene Pheromone Dispenser for Mating Disruption of Coding Moth (Lepidoptera: Torrticidae)", *J. Econ. Entomol.*, 85(3), pp. 910–917.

Brown, DF., & McDonough, L.M., (1986), "Insect Sex Pheromones: Formulations to Increase the Stability of Conjugated Dienes", *J. Econ. Entomol.*, 79(4), pp. 922–927.

Charmillot, P.J. & Bloesch B., (1987), "La Technique de Confusion Sexuelle: un Moyen Spécifique de Lutte Contre le Carpocapse *Cydia pomonella*", *L. Rev. Suisse Vitic. Aboric. Hortic.*, 19(2), pp. 129–138, (Translation of abstract will be provided upon request).

Duan, J.J., et al., (1991), "Advancements in Second-stage Apple IPM: Combination of Fruit and Food Odor to Increase Captures of Apple Maggot Flies on Sticky Red Spheres", *Fruit Notes*, pp. 4–6.

Mani, E., et al., (1984), "Bekämpfung des Apfelwicklers (*Cydia pomonella* L.) mit der Verwirrungsmethode in Einer Obstanlage im Bundner Rheintal: 1979–81", *Mitt. Schweiz. Entomol. Ges.*, 57, pp. 341–348, (Translation of abstract will be provided upon request).

Moffitt, H.R., & Westigard, P.H., (1984), "Suppression of the Coding Moth (Lepidoptera: Tortricidae) Population on Pears in Southern Oregon Through Mating Disruption with Sex Pheromone", *J. Econ. Entomol.*, 77(6), pp. 1513–1519.

Reissig, W.H., et al., (1984), "Insect Management in Disease-Resistant Dwarf and Semi-Dwarf Apple Trees", *Environ. Entomol.*, 13(5), pp. 1201–1207.

*Primary Examiner*—Neil S. Levy
*Attorney, Agent, or Firm*—Lahive & Cockfield, LLP

[57] ABSTRACT

The present invention features a method and composition for attracting a target insect to a selected location. The invention is based on the discovery that negatively charged chitosan polymers, e.g., NOCC, have advantageous properties for use in a semiochemical delivery system for releasing a volatile semiochemical at a substantially sustained rate over an extended period of time to attract a target insect to a selected location. The present invention may be used for monitoring a target insect by capturing the insect. Alternatively, the present invention may be used for the management of a target insect by disrupting mating patterns of such insects.

15 Claims, 3 Drawing Sheets

NEGATIVELY CHARGED CHITOSAN DERIVATIVE SEMIOCHEMICAL DELIVERY SYSTEM

BACKGROUND OF THE INVENTION

The present invention relates to semiochemical delivery systems useful for attracting a target insect to a selected location and to disrupt normal insect mating behavior. The invention provides a negatively charged chitosan derivative, e.g., NOCC-based, semiochemical delivery system which releases a semiochemical material into the atmosphere at a sustained rate over an extended period of time.

Semiochemicals are the broad category of naturally occurring compounds that produce odors which play a key role in the lives of insects, assisting them to locate food, water, and mating partners, and also serve as warning signals of impending danger. For example, certain semiochemicals such as sex-pheromones are species-specific communication chemicals which attract mating partners. Sex pheromones are emitted by either male or female insects. Other semiochemicals such as allomones are inter-species compounds that are primarily beneficial to the species releasing the odor. For example, allomones released from flower blossoms attract pollinators, and such pollination benefits the flower while the pollen provides a food source to the pollinator.

The ability of semiochemicals to influence insect behavior is also interrelated with environmental conditions such as temperature, humidity, barometric pressure, wind movement, and exposure to sunlight. In addition, the ability of semiochemicals to influence insect behavior is dependent upon biological factors associated with the insect population such as insect age, and gender ratio and distribution.

Controlled release of semiochemicals to influence insect behavior is a potentially valuable tool for agricultural management. For example, controlled release of semiochemicals at a sustained rate over an extended period of time may potentially be used to monitor an insect population by capturing insects over an entire growing season. In addition, such controlled release of semiochemicals may potentially be used as a biopesticide to disrupt mating patterns of insects harmful to a specific agricultural or forestry product.

Researchers have evaluated several types of semiochemical delivery systems for the controlled release of semiochemicals, but problems related to short field life, application difficulty and inconsistent release rates under field conditions have decreased efficiency. Dispensers evaluated for semiochemical delivery include rubber tubing, see Mani et al., "Bekämpfung des Apfelwicklers (*Cydia pomonella* L.) mit der Verwirrungsmethode in Einer Obstanlage im Bundner Rheintal", 1979–81 Mitt. Schweiz. Entomol. Ges. 57, pp. 341–348 (1984); microcapsules, see Charmillot & Bloesch, "La Technique de Confusion Sexuelle: un Moyen Spécifique de Lutte Contre le Carpocapse *Cydia pomonella*", L. Rev. Suisse Vitic. Arboric. Hortic. 19, pp. 129–138 (1987); laminated plastic flakes, see Charmillot & Bloesch, id; Audemard, "Confusion Sexuelle avec des Phéromones en Europe De L'Ouest", Agric. Ecosyst. Environ. 21, pp. 101–110 (1988); hollow fiber tapes, see Reissig et al., "Insect Management in Disease-Resistant Dwarf and Semi-Dwarf Apple Trees", Environ. Entomol. 13, pp. 1201–1207 (1984); chopped hollow fibers, see Moffitt & Westigard, "Suppression of the Codling Moth (Lepidoptera; Tortricidae) Population on Pears in Southern Oregon Through Mating Disruption with Sex Pheromone", J. Econ. Entomol. 77, pp. 1513–1519 (1984); and polyethylene stripes, see Brown et al., "Insect Sex Pheromones: Formulations to Increase the Stability of Conjugated Dienes", J. Econ. Entomol. 79, pp. 922–927 (1986).

Researchers have also experimented with different combinations of semiochemicals to increase the efficiency of semiochemical delivery systems for the controlled release of semiochemicals. For example, researchers identified that spheres baited with a combination of semiochemicals relating to mating and feeding attracted more insects compared with spheres baited with either a mating or a feeding semiochemical alone. However, semiochemical delivery systems have the tendency to break down under conditions of high humidity. See J. J. Duan et al., *Advancements in Second-stage Apple IPM: Combination of Fruit and Food Odor to Increase Captures of apple Maggot Flies on Sticky Red Spheres,* Fruit Notes 4, 6 (Fall, 1991).

Negatively charged chitosan derivative materials may be excellent candidates for the controlled release of semiochemicals because of their unique properties. In particular, a novel derivative of carboxymethylchitosan, N,O-carboxymethylchitosan ("NOCC") disclosed by Hayes in U.S. Pat. No. 4,619,995 (the disclosure which is incorporated herein by reference), which has carboxymethyl substitutes on some of both the amino and primary hydroxyl site of the glucosamine units of the chitosan structure may be used in an uncrossed linked form as a solution, or may be covalently crosslinked or non-covalently complexed into a gel. Thus, it may be possible that the various forms of NOCC allow application of the material in different forms to provide semiochemical delivery systems tailored to specific applications. In addition, semiochemicals that possess aldehyde or amino groups may be bonded directly to the NOCC polymer and the release rate controlled by the slow breakdown of the imine bond. Further, a surfactant or oil may be added as an agent which assists in the maintenance of semiochemicals in the gel, or substitutents with surfactant function can be chemically bonded to the polymer chain. Either approach alters the rate of release of the semiochemical. Since NOCC polymers are biodegradable to simple sugars, there is no polluting residue after the NOCC polymers have released the semiochemicals. Finally, chitin, which may be chemically modified to form NOCC polymers, can be cheaply obtained from the shells of crustaceans and many insects, waste products that would otherwise have to be disposed. Thus, negatively charged chitosan derivative materials, and NOCC in particular, present advantageous properties for use in insect management, because of their unique properties and low cost.

Accordingly, an object of the present invention is to provide a method of using a negatively charged chitosan derivative, e.g., NOCC-based, semiochemical delivery system to attract a target insect to a selected location.

Another object of the invention is to provide a method of using a negatively charged chitosan derivative, e.g., NOCC-based, semiochemical delivery system to monitor a target insect population by attracting the target insect to a selected location.

A further object of the invention is to provide a method of using a negatively charged chitosan derivative semiochemical, e.g., NOCC-based, delivery system to disrupt the mating patterns of a target insect by providing a sufficient level of the semiochemical over a diffuse area.

A still further object of the invention is to provide a method of using a negatively charged chitosan derivative semiochemical, e.g., NOCC-based, delivery system to release a volatile semiochemical at a sustained rate over an extended period of time to attract a target insect to a selected location or to disrupt mating behavior.

A still further object of the invention is to provide a negatively charged chitosan derivative, e.g., NOCC-based, semiochemical delivery system which releases a volatile semiochemical at a sustained rate over an extended period of time to attract a target insect to a selected location or to disrupt mating behavior.

These and other objects and features of the invention will be apparent from the following description and the drawing.

SUMMARY OF THE INVENTION

The present invention features a method and composition for attracting a target insect to a selected location, or for disrupting normal insect mating behavior. The invention is based on the discovery that selected negatively charged chitosan polymers have advantageous properties for use in a semiochemical delivery system for releasing a volatile semiochemical at a substantially sustained rate over an extended period of time.

The method of the invention includes providing a negatively charged chitosan derivative, e.g., NOCC-based, delivery system at a selected location, where the negatively charged chitosan derivative semiochemical delivery system with a volatile semiochemical entrapped therein is selected to provide a substantially sustained release of the volatile semiochemical over an extended period of time. The negatively charged chitosan derivative semiochemical delivery system then releases the volatile semiochemical from the delivery system into the atmosphere at a sustained rate over an extended period of time to attract a target insect to a selected location or to disrupt normal mating behavior. In the later case, the rate of semiochemical release should be sufficient to achieve a level of pheromone in the tree canopy to interfere with normal chemical communication between males and females, which reduces the frequency of mating.

In a preferred embodiment, the negatively charged chitosan derivative semiochemical delivery system is a NOCC polymer. An application device such as a syringe, a squeezable tube or a caulking gun can be filled with the NOCC-semiochemical delivery system, and the delivery system may be distributed in a holder, such as a Pherocon card or a Pherocon AM trap, which is placed at the selected location, or applied directly to a tree or other support located in the field or orchard. The NOCC polymer can be provided in the form of a covalently cross-linked gel using an organic cross-linking organic agent such as glyoxal or some other form such as a non-covalent complex using a complexing agent such as a multivalent ion, e.g., calcium ion, or a polymeric material. Other non-semiochemical constituents of the gel may include a surfactant, particularly a nonionic surfactant such as a polyoxyethylene sorbitan fatty acid ester, glycerol, water and a lipid such as vegetable or silicone oil. The surfactant and/or lipid act as stabilizers for the semiochemical in the gel. A preferred semiochemical is a pheromone such as codling moth sex pheromone E, E-8, 10-Dodecadiene-1-ol. The term "semiochemical", as used herein, encompasses sex pheromones, alarm pheromones, kairomones, allomones, and the like. The semiochemical delivery system may be used and selected to target any particular insect, e.g., an insect selected from a group consisting of codling moth *Cydia pomonella*, apple maggot *Rhagoletis pomonella*, and blueberry maggot adult *Rhagoletis mendax* Curran (L.)

The invention further features a composition for providing substantially sustained release of a semiochemical into the atmosphere at ambient temperature to attract a target insect to a selected location or to disrupt mating. The composition includes a negatively charged chitosan derivative, e.g., NOCC-based, delivery system having entrapped therein a semiochemical which has a substantial vapor pressure at an ambient temperature and which can be released from the delivery system at a sustained rate over an extended period of time. The NOCC-based system previously described is preferred. In some circumstances, the addition of a solid absorbent can help retain volatiles to assist in sustained release. Preferred solid absorbents are chitosan, finely divided (and possibly activated) charcoal, and molecular sieves which can be added to the NOCC gel.

Further aspects of the invention will be apparent from the following detailed description of the invention and the drawing.

DETAILED DESCRIPTION OF THE INVENTION

Figure 1:
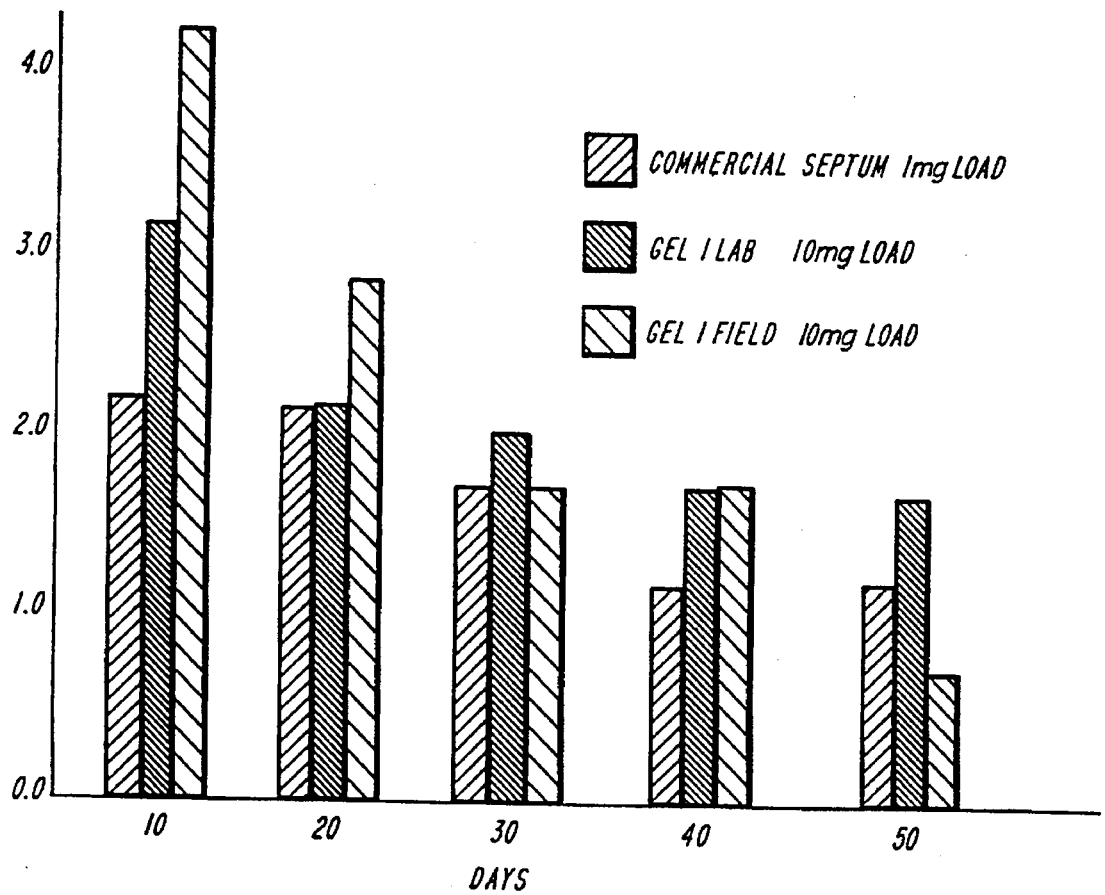
FIG. 1 is a bar graph showing the semiochemical release rates for a NOCC gel formulation in comparison with those release rates for a commercial septum under laboratory and field conditions over time.
Figure 2:
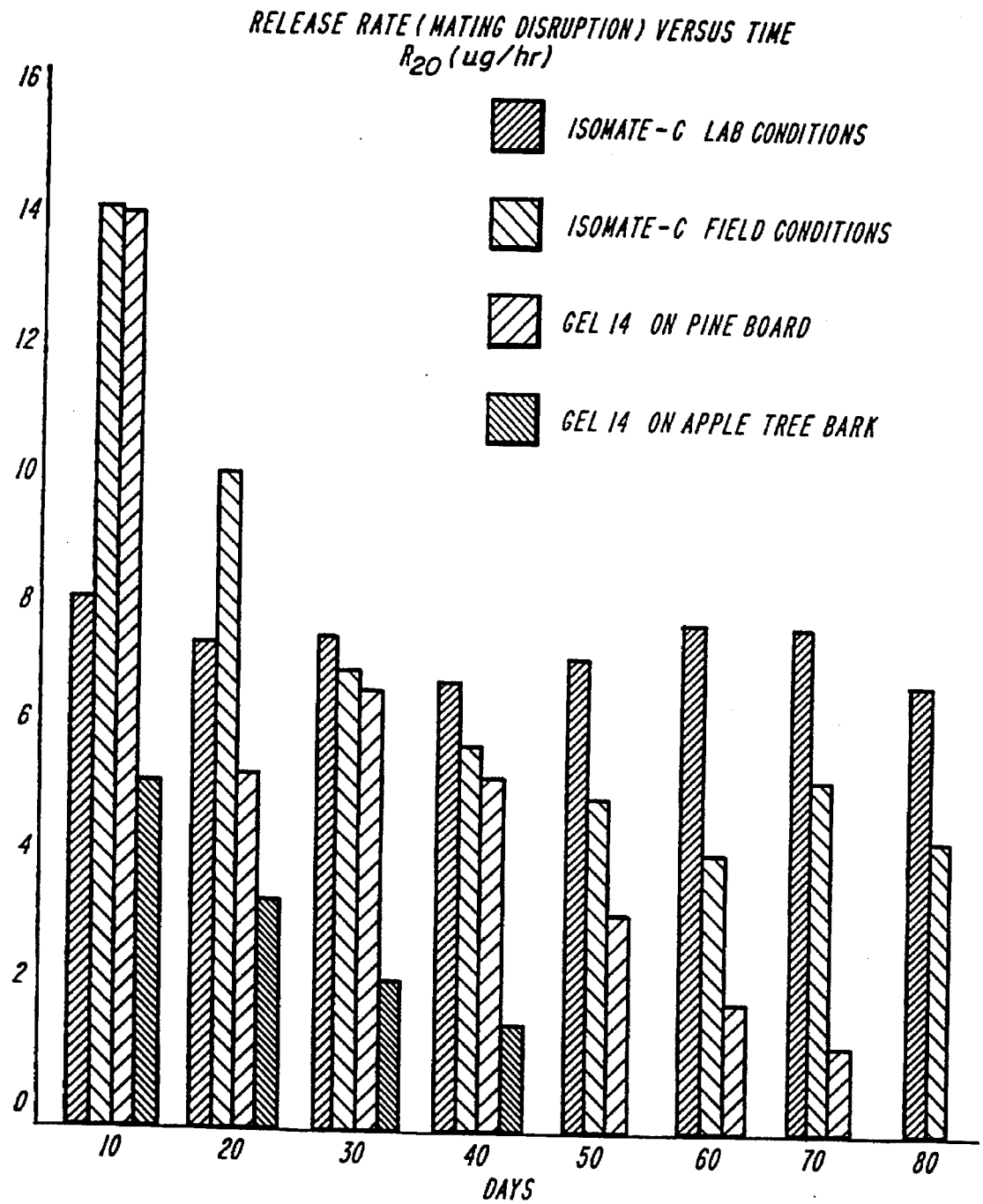
FIG. 2 is a bar graph showing the semiochemical release rates for a NOCC gel on pine bark and apple bark substrates in comparison with those release rates for commercially available ISOMATE-C dispensers operating under laboratory and field conditions.

The present invention provides a method and composition for attracting a target insect to a selected location or disrupting mating patterns through the use of a negatively charged chitosan derivative delivery system which releases a semiochemical at a sustained rate over an extended period for time. In a preferred embodiment, the negatively charged chitosan derivative is NOCC. The form of the negatively charged chitosan derivative delivery system, i.e., gel, the application device, the holder for distribution (if any), and the semiochemical and non-semiochemical constituents are selected to tailor the semiochemical release to a particular target insect and behavior, i.e., insect mating. The negatively charged chitosan derivative may be bonded directly to semiochemicals that possess aldehyde or amino groups, and the release rate of the semiochemicals may be controlled by the slow breakdown of the imine bond. Alternatively, the semiochemical may be entrapped in a gel or complex of the polymer, possibly using a stabilizer such as a surfactant or lipid, and solid absorbent as well. The negatively charged chitosan derivative may be easily and cheaply obtained from the chemical modification of chitin from the shells of crustaceans.

In some embodiments, e.g., as an insect trap, the NOCC based system is placed in a holder and is used to attract the insects to a particular location. In other embodiments, e.g., as a mating disruption system, the material may be sticky and adhered directly to a tree or other tall object. The mating disruption is then accomplished by the release of sufficient semiochemical that the tree canopy as a whole is inundated with the semiochemical which inhibits the insects from finding mates and therefore reduces the frequency of mating.

The following non-limiting examples will further elucidate the invention.

EXAMPLE 1

This example shows that the release rate of the present invention NOCC-based semiochemical delivery system is temperature dependent over a 20° to 40° C. temperature range.

NOCC was prepared in a gel formulation referred to as GEL 1. GEL 1 was prepared from the following components according to the weight percentages shown below:

TABLE 1

| Component | Weight Percentage |
| --- | --- |
| NOCC | 0.9% |
| TWEEN 20 | 8% |
| Glycerol | 50% |
| Glyoxal | 0.05% |
| Water | 41% |
| Pheromone was added in the amount of 20 mg/g GEL 1. | |

The preferred procedure for GEL 1 manufacture was a three component system. Component 1 was prepared by dissolving 17.8 g of TWEEN 20 in 100 ml of water. NOCC (2 g) were added and dissolved by stirring for ½ hour. The solution was then filtered through a fine screen. Component 2 was prepared by dispersing 400 mg of Pheromone in 5 ml of warm glycerol in a 10 ml volumetric flask. The mixture was diluted to 10 ml with glycerol. Component 3 was prepared by diluting 2.5 g of 40% (w/v) glyoxal with 100 ml of water.

Ten grams of GEL 1 were prepared by adding 5 g of the Component 2 to 4.5 g of the Component 1 and mixing thoroughly on a magnetic stirrer. The Component 3 (0.5 grams) was added and the mixture was stirred homogeneously for several minutes. The resulting gel mixture was then poured into application tubes, such as a syringe, squeezable tube or a caulking gun, and allowed to cure at least overnight before application to the insect traps. The procedure made enough gel to bait 20 traps at 0.5 g gel/trap load.

The insect traps with GEL 1 were sampled on Day 1 and Day 14 of a 14 day testing period for the trial. A freshly prepared commercial septum lure and a two week aged commercial septum lure were sampled for comparison.

TABLE 2

| | Release Rate (µg/hr) Versus Temperature | | | |
| --- | --- | --- | --- | --- |
| Sample | 21° C. | 25° C. | 30° C. | 40° C. |
| GEL 1 - Fresh | 0.86 | 1.0 | 2.2 | 4.6 |
| Septum - Fresh | 0.40 | 1.3 | 0.96 | 3.2 |
| GEL 1 - Day 14 | 0.27 | 0.20 | 0.50 | 2.8 |
| Septum - Day 14 | ND | 0.08 | 0.40 | 2.1 |

ND = Not Detectable < 0.05 µg/hr

The results of the trial presented in Table 2 show that the release rate of GEL 1 increased with increasing temperature over a 20° to 40° C. temperature range for either fresh or aged samples.

EXAMPLE 2

This example shows the release rate of GEL 1 over time.

The release rate of pheromone at 40° C. for GEL 1 and a commercial septum lure were monitored over a 50 day testing period. These samples were kept at room temperature, out of direct sunlight, in an area subject to occasional drafts. Samples of GEL 1 were placed in traps in an orchard in mid-June and removed at regular intervals for analysis.

The results of the trial presented in FIG. 1 show that the release rates of the pheromone from GEL 1 and from the commercial septum lure were comparable over 50 days.

EXAMPLE 3

This example shows that other formulations within the scope of the invention may be made which provide certain advantageous properties. GEL 1 does not adhere to wood, and such adherence is necessary for application of the gel to provide disruption of insect mating patterns in a tree canopy.

Samples of GEL 1 were placed on wood in a field and found to fall within days of the application. Modification to the gel matrix was required to insure that the present invention's NOCC-based semiochemical delivery system would remain intact upon application in a tree canopy.

Gels containing various proportion of glycerol, TWEEN 20, vegetable oil, and salts were prepared for weathering tests without pheromones. A 0.5 g sample was applied to a spruce board as an 8 mm by 250 mm bead, extruded from a 10 ml syringe. The gel was allowed to cure overnight with the board in an upright position. The following day, the beads of gel were subjected to a continuous spray of water from a garden sprinkler to test adhesion.

Observations indicated that the presence of TWEEN 20 (2 to 8%), sodium chloride (0.3%), or sodium acetate (0.5%) caused the gel to wash away within minutes of application. Thus, it was determined that no gel matrix containing any of these ingredients was acceptable for application to a tree canopy because they failed to adhere to wood. It was further determined that concentrations of glycerol above 10% caused deterioration of the gel after about 10 minutes. Gels containing oil at greater than 5% also failed within 10 to 20 minutes.

EXAMPLE 4

This example shows that Gel 14, an alternative NOCC-based semiochemical delivery system gel formulation, may be used for the disruption of insect mating patterns. GEL 14 adheres to wood and other surfaces.

GEL 14 was prepared from the following materials according to the weight percentages shown below:

TABLE 3

| Component | Weight Percentage |
| --- | --- |
| NOCC | 0.9% |
| Vegetable Oil | 4% |
| Glycerol | 8% |
| Glyoxal | 0.05% |
| Water | 87% |
| Pheromone was added in the amount of 20 mg/g GEL 14 for a 100 mg/5 g pheromone load. | |

A three component system similar to Example 1 was used. Component 1 was prepared by dissolving 1.1 g of NOCC in 100 ml of water. The mixture was stirred for ½ hour and then filtered through a fine screen. Component 2 was prepared by dispersing 200 mg of pheromone in 0.8 g of warm glycerol containing 0.4 g of vegetable oil in a small beaker. Component 3 was prepared by diluting 2.5 g of 40% (w/v) glyoxal with 100 ml of water.

Ten grams of gel for two 5 g applications were prepared by adding 8.8 g of Component 1 to Component 2 and mixing thoroughly on a magnetic stirrer. Component 3 (0.5 g) was added and the mixture was covered and gently stirred overnight. The gel mixture was then allowed to cure at least one additional night before pouring into application tubes.

A 20 cm$^2$ application on different surfaces was used to measure release rate of pheromone at approximately 20° C. The results of the tests presented in Table 4 show that the gel adhered to different surfaces and the pheromone was released over a 7 day period from GEL 14.

TABLE 4

Release Rate of Pheromone in Gel From Different Surfaces

| Surface | Days | $R_{20}$ (μg/hr) |
| --- | --- | --- |
| Metal | 7 | 3.0 |
| Wood (smooth spruce) | 7 | 11.7 |
| Apple Tree (with bark) | 8 | 5.4 |

EXAMPLE 5

This example shows that the semiochemical release rate from GEL 14 can be modified by changing the semiochemical load.

A gel formulation was prepared containing one half of the amount of oil (2%) and one half the amount of pheromone as original GEL 14 to determine whether the semiochemical release rate would be effected.

The results shown in Table 5 indicate a decreased release rate for the NOCC gels containing lower amounts of oil and pheromone. The lower amount of pheromone was most likely responsible for the decreased release rate.

TABLE 5

Release Rate Versus Oil Concentration

| | | $R_{20}$ (μg/hr) | | |
| --- | --- | --- | --- | --- |
| % Oil | mg Pheromone | Day 1 | Day 4 | Day 6 |
| 4 | 100 | — | 10.8 | 8.2 |
| 2 | 50 | 5.7 | 4.8 | 3.0 |

EXAMPLE 6

This example shows the ability of the NOCC-based semiochemical delivery system to prevent damage to the apple product of an apple orchard by disrupting the mating of codling moths which feed on the apples.

Center and edge rows of one half of a 0.75 ha, five year old Macintosh apple orchard were treated with ISOMATE-C and the other half were treated with the NOCC-based semiochemical delivery system. The rate of application was equivalent to 500 ISOMATE-C twist ties per ha.

Figure 3:
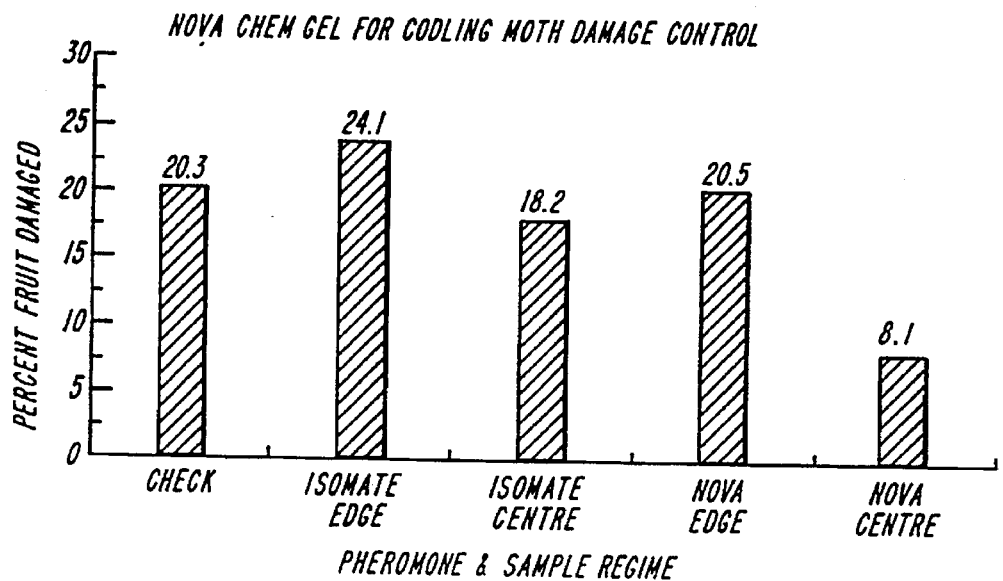
FIG. 3 is a bar graph showing a comparison between the percentage of fruit damaged following a treatment with a NOCC-based semiochemical delivery system and the percentage of fruit damaged following a treatment of a commercially available ISOMATE-C delivery system.

FIG. 3 shows the percentage of fruit damaged after the treatment applied to edge rows and center rows during a 50 day summer testing period.

The high percentage of fruit damage was a consequence of two factors. First, a light crop was induced by dry weather. Few fruit resulted in intensified egg laying on or near the few host sites, i.e., apples, available. Second, trap capture reflected a modest interior orchard population of codling moth that was supplemented by gravid females immigrating from the orchard exterior into the interior of the orchard. Hence, edge rows experienced more damage than rows at the center of the orchard. Notwithstanding, the treatment with the NOCC delivery system of the present invention resulted in greater mating disruption, and hence fewer fruit damaged, than that of the ISOMATE-C system for both the edge and center rows of the orchard.

EXAMPLE 7

This example shows the ability of the NOCC-based semiochemical delivery system to monitor blueberry maggot flies. Commercial lure systems and the NOCC-based semiochemical delivery system were used to capture blueberry maggot flies in field trials conducted over a twenty day summer testing period.

Figure 4:
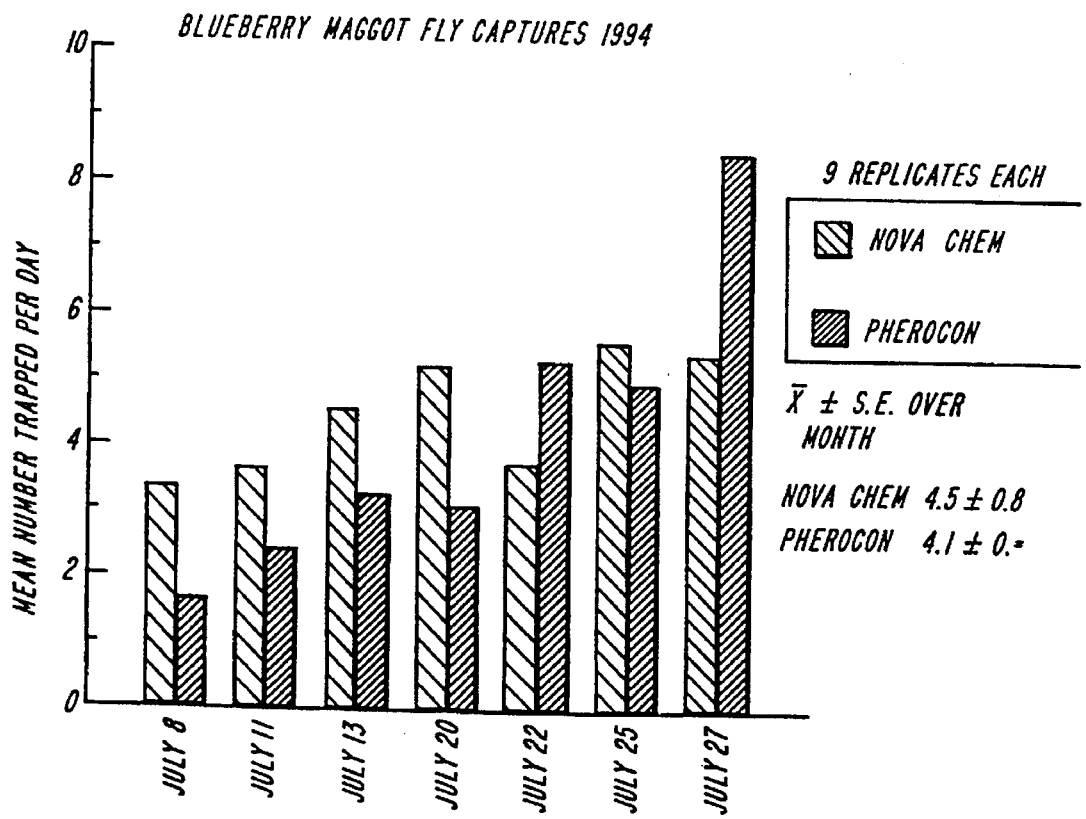
FIG. 4 is a bar graph showing a comparison between the mean number of blueberry maggot flies captured with a NOCC-based semiochemical delivery system and the mean number of blueberry maggot flies captured with a commercially available Pherocon AM trap lure system.

FIG. 4 shows the mean number of blueberry maggot flies captured with a commercial lure system (a Pherocon AM trap) in comparison with the NOCC-based semiochemical delivery system during this testing period. According to these results, the NOCC-based semiochemical delivery system was as effective as the commercial lure system.

In a related experiment, six commercial low bush blueberry fields of approximately 4 to 10 ha in size in the Parrsboro area of Nova Scotia served as the test sites for field trials conducted for two summer months. Conventionally baited Pherocon traps were compared with Pherocon traps baited with the NOCC-based semiochemical delivery system composition. Adult *R. mendax* capture rates were monitored three times weekly. The conventionally baited Pherocon traps were replaced after three weeks. A comparison of cumulative captures on each type of trap was conducted using regression analysis with a logic model. Mean counts per trap type were analyzed to determine the relative efficacy of the traps.

TABLE 6

Mean Seasonal Adult *R. mendax* Captures on Nine Sets of Paired Traps Set in Commercial Lowbush Blueberry Fields in Nova Scotia

| Treatment | *R. Mendax* adult captures (#) |
| --- | --- |
| Conventional baited Pherocon trap | 53.0 |
| Slow release baited Pherocon trap | 53.4 |

The Pherocon traps baited with the NOCC-based semiochemical delivery system composition were as effective as the conventionally baited Pherocon traps in capturing adult *R. mendax* in commercial low bush blueberry fields. This was despite the fact that the commercial traps had to be replaced after three weeks while only a single application of the NOCC based delivery system was used. Table 6 shows that the mean number of captures per trap were similar.

EXAMPLE 8

This example shows the ability of the NOCC-based semiochemical delivery system to monitor apple maggot flies in apple orchards.

Field trials were conducted utilizing Pherocon AM traps with protein and apple volatiles, Pherocon AM traps baited with a NOCC-based semiochemical delivery system, Pherocon AM traps baited with the NOCC-based semiochemical delivery system including apple volatiles, Pherocon AM trap with protein (but no volatiles) and red spheres baited with Ladd Inc. apple volatiles. Test site 'A' was a 1.5 ha apple orchard having Macintosh and Ida Red apples. Test site 'B' was a nine year old 2.0 ha orchard of Macintosh apples. Traps were hung 1.5 meters above ground level on a southeast exposure. Each of the five treatments tested was replicated in a completely randomized design with 8 meters between traps within replicates and 16 meters between each of the replicates. Traps were initially set in mid-summer and subsequently checked weekly for maggot flies. Analysis of variance and separation of the means caught by Turkey's pairwise comparison was conducted on the mean number of flies caught per trap per sample day.

TABLE 7

Apple Maggot Fly Response to Select Trap/Lure Combinations (July 1994)

| Trap/Lure | Mean (Standard Error) capture rate per trap day | | |
|---|---|---|---|
| | Males | Females | Total (combined sexes) |
| Site 'A' | | | |
| Red sphere | 1.09 (.26) | 1.56 (.36) | 2.66 (.60) |
| Pherocon card NOCC + protein | 0.13 (.06) | 0.16 (.08) | 0.28 (.10) |
| NOCC + protein + apple volatiles | 0.09 (.07) | 0.50 (.17) | 0.59 (.22) |
| Pherocon card + protein | 0 | 0.06 (.04) | 0.06 (.04) |
| Pherocon card + protein + apple volatiles | 0.03 (.03) | 0.28 (.14) | 0.31 (.16) |
| Site 'B' | | | |
| Red sphere | 0.92 (.29) | 0.88 (.31) | 1.79 (.60) |
| NOCC + protein | 0.04 (04) | 0.08 (.06) | 0.13 (.07) |
| NOCC + protein + apple volatiles | 0.29 (.09) | .033 (.13) | 0.63 (.18) |
| Pherocon card + protein | 0 | 0.21 (.08) | 0.21 (.08) |
| Pherocon card + protein + apple volatiles | 0.17 (.08) | 0.29 (.13) | 0.46 (.18) |

The NOCC-based semiochemical delivery system achieved as effective capture rates as the Pherocon AM traps. Table 7 shows that the NOCC-based semiochemical delivery system equaled the capture rates of all the treatments except for the red spheres, which outperformed all the trap combinations. Notwithstanding, red spheres are not widely accepted by orchardists.

EXAMPLE 9

This example shows that the addition of absorbents, e.g., particulate chitosan or activated charcoal, can provide a "reservoir" of volatiles useful to assist in sustained release of the volatile semiochemical over time. For some semiochemicals such as apple volatiles, a high load is required which can cause instability in gels containing oil, glycerol or ionic surfactants. While a non-ionic surfactants such as TWEEN 20 can be used, a solid absorbent such as finely ground chitosan powder has advantageous properties to retain the volatiles and extend the field life of the device. Table 9 shows the components and weight percent for an absorbent containing NOCC gel.

TABLE 9

| Component | Weight Percentage |
|---|---|
| NOCC polymer | 1% |
| Chitosan adsorbent | 10% |
| Glycerol | 15% |
| TWEEN 20 | 10% |
| Apple volatiles | 100 mg |
| Glyoxal | 0.05% |
| Water | 64% |

A commercial septum (LADD, Inc.) containing apple volatiles was compared with a device having a gel of the formula shown in Table 9 incorporated therein. While the initial release rate of the volatiles from the commercial septum was higher than the NOCC gel, after one week the release rate was less than that for the chitosan containing NOCC gel. The device having the chitosan containing NOCC gel maintained a substantially constant release of volatiles for one month, while the commercial product was no longer releasing detectable levels of the volatiles after two weeks. In another test, the TWEEN 20 was determined to be unnecessary.

EXAMPLE 10

In this example, the use of an ammonium salt, ammonium bicarbonate, as an attractant to indicate the presence of protein was tested. Maggot lures often include ammonium and the simplest device is based on volatile ammonium salts. Ammonium bicarbonate was found to release ammonia at a significant rate and for a sustained period. This release was extended by loading ammonium bicarbonate into a plastic container and placing a layer of NOCC gel over the salt surface. Release rates of greater than 2 mg/hr could be sustained for more than thirty days.

This ammonium bicarbonate release was then used in traps for both apple and blueberry maggots. Apple volatiles were also added and the gels containing chitosan described in Example 9, as well those without chitosan, were tested. It was found that using finely ground chitosan in the gel would double the effective time of the lures.

The foregoing examples illustrate the effectiveness of the present invention. These examples are merely exemplary and those skilled in the art will be able to determine other modifications to the described procedures which fall within the scope of the invention. For example, the gel used in the invention can be of higher or lower concentration by modifying the amount of, or type of, cross-linking or complexing agent. Accordingly, the invention is defined by the following claims and equivalents thereof.

We claim:

1. A composition for providing sustained release of a volatile semiochemical into the atmosphere at ambient temperature; said composition comprising a N,O-carboxymethylchitosan (NOCC) semiochemical gel system having entrapped therein a semiochemical which has a substantial vapor pressure at an ambient temperature such that said semiochemical is released from said NOCC at a sustained rate over an extended time period.

2. The composition of claim 1 wherein said system further comprises an absorbent.

3. The composition of claim 2, wherein said absorbent is selected from the group consisting of particulate chitosan, and particulate charcoal.

4. The composition of claim 1 wherein said NOCC gel comprises a covalently cross-linked NOCC gel.

5. The composition of claim 4 wherein said covalently cross-linked NOCC gel is comprises an organic covalently cross-linked NOCC gel.

6. The composition of claim 5 wherein said organic covalently cross-linked NOCC gel is cross-linked by glyoxal.

7. The composition of claim 1 wherein said NOCC gel comprises a non-covalently complexed NOCC gel.

8. The composition of claim 7 wherein said complexed NOCC gel is complexed by a multivalent ion.

9. The composition of claim 1 wherein said semiochemical comprises a pheromone.

10. The composition of claim 1 wherein said semiochemical is directed toward an insect selected from a group consisting of codling moth *Cydia pomonella*, apple maggot *Rhagoletis pomonella*, blueberry maggot adult *Rhagoletis mendax* Curran (L.).

11. The composition of claim 7 wherein said system comprises a surfactant.

12. The composition of claim 11 wherein said surfactant comprises a polyoxyethylene sorbitan ester.

13. The composition of claim 1 wherein said system comprises glycerol.

14. The composition of claim 1 wherein said system comprises a lipid.

15. The composition of claim 14 wherein said lipid comprises an oil.

* * * * *